US005456697A

United States Patent [19]
Chesterfield et al.

[11] Patent Number: 5,456,697
[45] Date of Patent: Oct. 10, 1995

[54] CABLED CORE AND BRAIDED SUTURE MADE THEREFROM

[75] Inventors: Michael P. Chesterfield, Norwalk; Ilya S. Koyfman, Orange; Donald S. Kaplan, Weston; Matthew E. Hermes, Easton, all of Conn.

[73] Assignee: United States Surgical Corporation, Norwalk, Conn.

[21] Appl. No.: 110,356

[22] Filed: Aug. 23, 1993

Related U.S. Application Data

[60] Division of Ser. No. 855,682, Jun. 17, 1992, Pat. No. 5,261,886, which is a continuation-in-part of Ser. No. 733,362, Jul. 19, 1991, abandoned, which is a continuation of Ser. No. 622,224, Dec. 5, 1990, abandoned, which is a continuation-in-part of Ser. No. 491,215, Mar. 9, 1990, Pat. No. 5,019,093, which is a continuation of Ser. No. 344,745, Apr. 28, 1989, abandoned, and a continuation-in-part of Ser. No. 227,699, Aug. 3, 1988, abandoned, and a continuation-in-part of Ser. No. 89,732, Aug. 26, 1987, abandoned.

[51] Int. Cl.$^6$ .................................................. A61B 17/04
[52] U.S. Cl. .............................. 606/228; 57/236; 57/237; 57/243; 57/204
[58] Field of Search ........................... 606/228–232; 57/12, 243, 204, 283, 293, 58, 49, 236, 237; 87/6, 8

[56] References Cited

U.S. PATENT DOCUMENTS

| | | |
|---|---|---|
| 3,125,095 | 3/1964 | Kaufman et al. . |
| 3,187,752 | 6/1965 | Glick . |
| 3,297,033 | 1/1967 | Schmitt et al. . |
| 3,359,983 | 12/1967 | Northey . |
| 3,371,069 | 2/1968 | Miyamae . |
| 3,443,451 | 5/1969 | Zieber, Jr. . |
| 3,565,077 | 2/1971 | Glick . |
| 3,772,420 | 11/1973 | Glick et al. . |
| 3,949,755 | 4/1976 | Vauquois . |
| 3,949,756 | 4/1976 | Ace . |
| 4,014,973 | 7/1973 | Thompson . |
| 4,024,871 | 5/1977 | Stephenson . |
| 4,043,344 | 8/1977 | Landi et al. . |
| 4,047,533 | 9/1977 | Perciaccante et al. . |
| 4,201,216 | 5/1980 | Mattei . |
| 4,204,542 | 5/1980 | Bokros et al. . |
| 4,321,038 | 3/1982 | Porteous . |
| 4,362,162 | 12/1982 | Nakajima et al. . |
| 4,523,591 | 6/1985 | Kaplan . |
| 4,546,769 | 10/1985 | Planck et al. . |
| 4,621,638 | 11/1986 | Silvestrini . |
| 4,712,553 | 12/1987 | MacGregor . |
| 4,759,069 | 9/1988 | Brennan et al. . |
| 4,792,336 | 12/1988 | Hlavacek et al. . |
| 4,793,131 | 12/1988 | Mizuno et al. ............................. 57/243 |
| 4,946,467 | 8/1990 | Ohi et al. . |
| 4,959,069 | 9/1990 | Brennan et al. . |
| 5,019,093 | 5/1991 | Kaplan et al. . |
| 5,080,159 | 1/1992 | Komai et al. ............................. 57/242 |

FOREIGN PATENT DOCUMENTS

| | | |
|---|---|---|
| 2949920 | 3/1981 | Germany . |
| 2082213 | 3/1982 | United Kingdom . |

OTHER PUBLICATIONS

1983 Annual Book of ASTM Standards vol. 10, pp. 65.
J. W. S. Hearle, Yarn Geometry, pp. 67–69 and 97 and 100.
V. A. Usenko, Mechanical Processing of Chemical Fibers (Technology of Twisting and Texturizing) Moscow, 1975, pp. 84–88.

*Primary Examiner*—Gary Jackson

[57] ABSTRACT

A braided suture possesses a cable core which resists any tendency to protrude through the surrounding braid structure.

39 Claims, No Drawings

CABLED CORE AND BRAIDED SUTURE MADE THEREFROM

This is a divisional of application Ser. No. 07/865,682 filed Jun. 17, 1992 now U.S. Pat. No. 5,261,886

CROSS REFERENCE TO RELATED APPLICATIONS

Which is a continuation-in-part of commonly assigned, U.S. patent application Ser. No. 07/733,362 filed Jul. 19, 1991, now abandoned, which is a continuation of commonly assigned, now abandoned U.S. patent application Ser. No. 07/623,224 filed Dec. 5, 1990, which is a continuation-in-part of U.S. application Ser. No. 491,215 filed Mar. 9, 1990 and now U.S. Pat. No. 5,019,093, which is a continuation of commonly assigned, now abandoned U.S. patent application Ser. No. 344,745 filed Apr. 28, 1989 as a continuation-in-part of commonly assigned, now abandoned, U.S. patent application Ser. No. 227,699 filed Aug. 3, 1988 as a continuation-in-part of commonly assigned, now abandoned, U.S. patent application Ser. No. 89,732 filed Aug. 26, 1987.

BACKGROUND OF THE INVENTION

This invention relates to a braided suture of improved construction featuring a cabled core component.

Sutures intended for the repair of body tissues must meet certain requirements: they must be substantially non-toxic, capable of being readily sterilized, they must have good tensile strength and have acceptable knot-tying and knot-holding characteristics and if the sutures are of the absorbable or biodegradable variety, the absorption or biodegradation of the suture must be closely controlled.

Sutures have been constructed from a wide variety of materials including surgical gut, silk, cotton, a polyolefin such as polypropylene, polyamide, polyglycolic acid, polyesters such as polyethylene terephthalate and glycolide-lactide copolymer, etc. Although the optimum structure of a suture is that of a monofilament, since certain materials of construction would provide a stiff monofilament suture lacking acceptable knot-tying and knot-holding properties, sutures manufactured from such materials are preferably provided as braided structures. Thus, for example, sutures manufactured from silk, polyamide, polyester and bioabsorbable glycolide-lactide are braided to provide optimum knot-tying and knot-holding properties.

Currently available braided suture products are acceptable in terms of their knot-tying and knot-holding properties. However, as removed from the package, they tend to be stiff and wiry and retain a "set" or "memory" such that at the time of use, it is usually necessary for the surgeon or assistant personnel to flex and stretch the suture to make it more readily handleable. Furthermore, the surfaces of known sutures are perceptibly rough. Thus, if one passes one's hand or fingers along the braid, surface irregularities will be readily detected. The result of this rough surface is that the suture will exhibit drag or chatter as it is drawn through tissue, characteristics which militate against smooth, neat, accurately placed wound approximation so necessary to excellence in surgical practice.

By way of overcoming the foregoing disadvantages which characterize commercially available braided sutures, U.S. Pat. No. 5,019,093 describes a braided suture of improved construction possessing a significantly greater number of sheath yarns for a given overall denier, the sheath yarns being fabricated from individual filaments of finer denier than filaments which are typical of known types of braided suture, the resulting improved suture exhibiting perceptibly improved flexibility and handling and reduced chatter and drag compared with braided sutures of known construction.

In all but the smallest size, the sutures of U.S. Pat. No. 5,019,093 can optionally be constructed around a filamentous core, a particularly advantageous feature in sutures of heavier denier. In some of these core-containing suture constructions, the larger number of sheath yarns in the braid may require a larger diameter core relative to that of a core of a similar braided suture constructed from fewer sheath yarns. However, a difficulty has been observed during the normal processing and handling of sutures possessing a somewhat larger core, namely, the core has a tendency in some cases to work through the surface sheath yarns. This "core popping" tendency can be diminished or eliminated by increasing the braid angle (the angle at which sheath yarns cross over each other in the braid). However, this solution to the problem of core popping can only come at the expense of surface smoothness of the suture since such smoothness decreases as the braid angle increases.

SUMMARY OF THE INVENTION

It is an object of the invention to provide a braided suture possessing a cabled multifilamentous core.

It is a particular object of the invention to provide such a suture possessing a greater number of sheath yarns, a finer denier for the individual filaments contained in an individual sheath yarn and a greater pick count (crossovers per linear inch) for a suture of any given overall denier while at the same time resisting any tendency of its core to penetrate through the outer surface of the suture.

In keeping with these and other objects of the invention, there is provided a braided suture possessing a cabled multifilamentous core component. The cabled core in accordance with the invention provides a balanced structure which remains straight and does not have a tendency to twist upon itself or protrude through the sheath. Individual yarns are twisted in a first direction, the "front" direction, and then multiple twisted yarns are twisted together in the reverse, "back", direction to form a cabled core. The cabled core should have a coefficient of twist, alpha, of at least about 24. It is also contemplated that multiple yarns may be plied together, i.e., aligned parallel to one another, with the plied yarns being front twisted and multiple plied yarns being back twisted to form the cabled core of the invention.

The term "suture" as used herein is intended to embrace both non-absorbable as well as the bioabsorbable varieties.

The term "braid" or "braided" as applied to the suture of this invention refers to an arrangement of discrete units, or bundles, denominated "sheath yarns", made up of individual filaments with individual sheath yarns interlocking or interlacing each other in a regular criss-cross pattern.

The term "cabled" as applied to the core component of the braided suture of this invention refers to a core made up of individual yarns each of which has been given a twist in one direction, the twisted yarns being combined to form a core which is then given a twist in a second, opposite direction.

The term "pick count" as applied to a braided suture construction refers to the number of crossovers of sheath yarns per linear inch of suture and, together with the overall denier of the suture, the denier of the individual filaments constituting a sheath yarn and the number of sheath yarns employed, defines the principal construction characteristics of a braided suture.

DESCRIPTION OF THE PREFERRED EMBODIMENTS

In a preferred embodiment, the braided suture of the present invention is fabricated from a bioabsorbable or biodegradable resin such as one derived from polyglycolic acid, glycolide, lactic acid, lactide, dioxanone, trimethylene carbonate, etc., and various combinations of these and related monomers. Sutures prepared from resins of this type are known in the art, e.g., as disclosed in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and, 4,523,591; U.K. Pat. No. 779,291; D. K. Gilding et al., "Biodegradable polymers for use in surgery—polyglycolic/poly(lactic acid) homo and co-polymers: 1, Polymer, Volume 20, pages 1459–1464 (1979), and D. F. Williams (ed.), *Biocompatibility of Clinical Implant Materials*, Vol. II, ch. 9: "Biodegradable Polymers" (1981).

Although the advantages of a cabled core in accordance with this invention, in particular, the resistance to "core popping" mentioned above, are conferred upon braided sutures generally which have been constructed with such a core, they are most fully realized in a braided suture constructed in accordance with the principles established in U.S. Pat. No. 5,019,093 referred to above. The defining characteristics of the braided suture of U.S. Pat. No. 5,019,093, apart from the material of its construction, are:

(1) overall suture denier;

(2) the pattern of the interlocking yarns expressed in pick count, which is to say, the number of crossovers of individual sheath yarns per linear inch of suture;

(3) the number of sheath yarns comprising the braid;

(4) the denier of the individual filaments comprising each sheath yarn; and, (5) the denier of the core.

(1) Overall Denier of the Suture

The overall denier of the preferred braided suture can vary from about 125 to about 4000. Within this range, the ranges of overall denier for particular sutures are: from above about 125 to about 200 denier; from above about 200 to about 300 denier; from above about 300 to about 500 denier; from above about 500 to about 800 denier; from above about 800 to about 1200 denier; from above about 1200 to about 2000 denier; and, from above about 2000 to about 4000 denier.

(2) Pattern of the interlocking Sheath Yarns (Pick count)

For a preferred suture of any range of overall denier, pick count can vary from about 50 to about 100 crossovers/inch with about 55–80 crossovers/inch being preferred. For preferred sutures constructed within any range of overall denier, as larger numbers of sheath yarns are employed, the pick-count for acceptable sutures will also increase within the above ranges. For a preferred suture of a particular range of denier and number of sheath yarns, pick count is advantageously established to achieve a balance in the properties desired. For preferred sutures of any specific denier range and number of sheath yarns, it is preferable to have as low a pick count as possible in order to achieve optimum surface smoothness.

(3) The Number of Sheath Yarns

In the preferred suture, the number of sheath yarns bears some relation to overall suture denier, the number generally increasing with the weight of the suture. Thus, across the range of suture weight (denier) indicated above, the preferred braided suture can be constructed with from about 4 up to as many as about 36 individual sheath yarns constructed from individual filaments having the deniers discussed below.

Table I below sets forth broad and preferred ranges for the numbers of sheath yarns which are suitable for the construction of preferred braided sutures of various ranges of overall denier. The pick counts of the preferred sutures vary from about 50 to about 100 and deniers of individual filaments vary from about 0.2 to about 6.0 for the broad range of number of sheath yarns and the pick counts vary from about 55 to about 80 and the deniers of individual filaments vary from about 0.8 to about 3.0, and advantageously from about 1.0 to about 1.8, for the preferred range of number of sheath yarns:

TABLE I

Number of Sheath Yarns Related to Suture Denier

| Overall Suture Denier | Suture Size | Number of Sheath Yarns (Broad Range) | Number of Sheath Yarns (Preferred Range) |
|---|---|---|---|
| greater than about 125 to about 200 | 6/0 | 4–16 | 6–14 |
| greater than about 200 to about 300 | 5/0 | 4–16 | 6–14 |
| greater than about 300 to about 500 | 4/0 | 10–20 | 12–14 |
| greater than about 500 to about 800 | 3/0 | 14–20 | 14–18 |
| greater than about 800 to about 1200 | 2/0 | 16–32 | 20–30 |
| greater than about 1200 to about 2000 | 0 | 20–36 | 24–32 |
| greater than about 2000 to about 4000 | 1,2 | 20–36 | 24–32 |

While the sheath yarns need not be twisted, it is generally preferred that they be provided with a twist so as to minimize snagging during braid construction. Alternatively, the sheath yarns can be air entangled.

(4) Individual Filament Denier

In the preferred sutures, the individual filaments comprising each sheath yarn can vary in weight. For smaller sutures, i.e. sutures having an overall suture denier of less than about 300, the individual sheath filaments can vary in weight from about 0.2 to about 3.0 denier, preferably from about 1.0 to about 1.8 denier. For larger sutures, i.e. sutures having an overall suture denier of greater than about 300, individual sheath filaments can vary in weight from about 0.2 to about 6.0 denier, preferably from about 0.8 to about 3.0 denier and more preferably from about 1.0 to about 1.8 denier. The number of such filaments present in a particular sheath yarn will depend on the overall denier of the suture as well as the number of sheath yarns utilized in the construction of the suture. Table II sets forth some typical numbers of filaments per sheath yarn for both the broad and preferred ranges of filament weight:

TABLE II

| Number of Filaments per Sheath Yarn | | |
|---|---|---|
| Approximate Minimum | Approximate Maximum | Filament Denier |
| 45 | 450 | 0.2 |
| 15 | 150 | 0.5 |
| 5 | 50 | 1.5 |
| 3 | 40 | 1.8 |
| 1 | 15 | 6.0 |

The individual filaments of the braided suture may be fabricated from a bioabsorbable polymer derived at least in part from one or more monomers selected from the group consisting of glycolic acid, glycolide, lactic acid, and lactide. Alternatively, the individual filaments may be fabricated from a non-absorbable material, e.g., cotton, silk, polyamide or polyolefin.

(5) Cabled Core

Whether or not provided as a component of the preferred type of braided suture construction described above or some other type of braided suture construction, the cabled core component of the braided suture herein is manufactured in a separate operation and is assembled from a plurality of individual yarns, e.g., from about 2 to about 1500, and preferably from 3 to about 1323 yarns. Each yarn comprising the core is given a twist in one direction, the "front" direction, the twisted yarns then being combined into a core which is then twisted in the opposite direction, the "back" direction, to provide the cabled core unit around which the remainder of the suture is constructed. Depending upon the material used to construct the core, it may be desirable to heat set and/or stretch the core in a known manner prior to final assembly of a braided suture incorporating the cabled core.

The denier of the individual yarns comprising the core is not particularly critical and can range in most cases from about 10 to about 100 and preferably from about 20 to about 70. The degree of twist which is applied to the individual yarns can vary widely with from about 200 to about 1500 turns per meter, and preferably, from about 240 to about 1200 turns per meter, generally providing good results.

The overall denier of the cabled core is, of course, determined by the number and individual deniers of the core yarns from which the core is constructed. For many suture constructions, core denier will range from about 20 to about 80 and preferably from about 25 to about 50 in the smallest size suture and from about 800 to about 2400 and preferably from about 1000 to about 2200 in the largest size suture. In order to increase the total core denier, it is contemplated that for larger suture cores it may be desirable to ply two or more yarns together, preferably before front twisting of the yarns.

The degree of reverse-direction or "back" twist should be determined for a particular suture construction so as to provide a balanced structure. Yarn-to-yarn twist levels can be compared through the "coefficient of twist function" alpha which is related to the helical angle. The coefficient of twist function can be calculated from the relationship $$\text{alpha} = \frac{K}{100} \sqrt{0.111D} \quad (1)$$

in which alpha is the coefficient of twist, K is the twist level in turns per meter and D is the denier of the resulting twisted product, e.g., twisted yarn or core. In other words, the coefficient of twist, alpha, is given by the product of yarn twist, K, and the square root of yarn count, i.e. mass per unit length or linear density. This coefficient of twist is also directly proportional to the helical or twist angle in yarns having the same solid density (or melt density), so alpha determined for one material can be applied to materials of the same density. Therefore, yarns having different deniers and the same coefficient of twist are geometrically similar, with the coefficient of twist thus being independent of the yarn denier.

The coefficient of twist in the cabled core construction is preferably at least about 24, more preferably at least about 28 and most preferably at least about 32.

To apply equal deformation to yarns of different denier, the coefficient of twist of the yarns should be the same. Yarns with higher deformation will have a higher coefficient of twist. For many braided suture constructions, the twist level in turns per meter of the cabled core component can range from about 200 to about 1500 turns per meter and preferably from about 240 to about 1200 turns per meter.

More specifically, the cabled core is constructed from a plurality of individual yarns possessing a first twist of from about 100 to about 1500 turns per meter, the twisted yarns being assembled into a core possessing a second, opposite twist of from about 100 to about 1200 turns per meter. Preferably, the individual yarns possess a first twist of from about 200 to about 1200 turns per meter, with the second opposite twist of the core being about 200 to about 1100 turns per meter.

In practice, once the desired overall core denier and denier of the yarns used to make the core are known, the coefficient of twist may be calculated for the overall core and individual yarns in order to approximate a balanced core structure. Equation (1) is first used to determine the degree of back twist, K, required to obtain a core of the desired overall core denier having a desired coefficient of twist, alpha, greater than 24. Using the same value for the coefficient of twist, equation (1) is then solved using the denier of the individual yarns to determine the approximate degree of front twist which must be applied to the individual yarns in order to obtain a balanced structure.

If multiple plied yarns are to be back-twisted to form the cabled core, the plied yarns are front twisted using equation (1) to determine the degree of twist required to obtain a balanced structure. After the cabled core is constructed, a simple loop test can be performed to determine whether a balanced structure has been achieved. In a common test used by applicants, a one meter length of core is sampled and the ends of the core sample are brought together with the remainder of the core allowed to hang and form a loop. If the loop remains substantially open, i.e., without twisting or with a twist less than 360°, the core structure is considered balanced. However, if the loop twists more than 360° (2 turns) in either direction, the structure is unbalanced and should be modified accordingly. It should be noted that if a cabled core has too much twist in one direction, then the loop will take a twist in the opposite direction. Thus, if the loop twists in a back direction (z), the amount of twist applied to the core or yarn in that back direction (z) should be increased, or the degree of twist in the opposite front direction(s) should be decreased. As will be appreciated, minor variations may be required in order to obtain the desired balanced core structure.

For the preferred suture constructions of U.S. Pat. No. 5,019,093, applicants have found that suture size 7/0 and smaller can be made without a core component, and that a core optionally can be included in sutures of size 6/0. Applicants have further found that cores for suture sizes 4/0, 5/0 and 6/0 can be constructed by twisting individual yarns in the front direction and then reverse-twisting individual yarns together to form the cabled core of the invention. For sutures of size 3/0 and larger, it is preferred to obtain the desired overall core denier by plying multiple yarns together, then front twisting and then back twisting the multiple plied yarns together to form the cabled core. In describing the cabled core, it is useful to identify the number of filaments in the structure in terms of the number of filaments in each yarn times the number of yarns plied together times the number of plied yarns which are back twisted together to form the cabled core. This terminology for the number of filaments in the core can be summarized in formula (2) as follows:

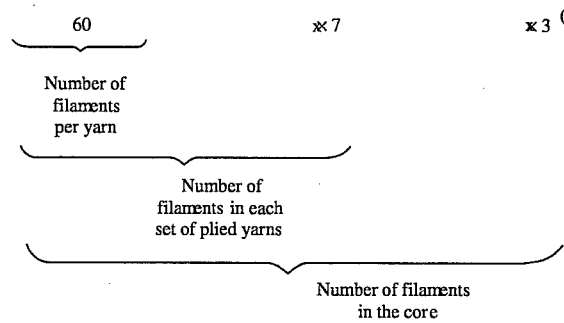

It will be understood that in the foregoing example, three sets of plied yarns are back twisted to form the core, with each front twisted plied yarn consisting of seven 60 filament yarns.

The following tables and examples set forth describe core and suture constructions suitable for making sutures in accordance with U.S. Pat. No. 5,019,093. It will be understood that the core construction may be varied within the scope of the invention for use in constructing sutures outside the scope of the foregoing patent.

Table III below provides some typical core deniers for sutures of various deniers:

TABLE III

Core Denier Related to Suture Denier

| Overall Suture Denier | Suture size | Denier of Cabled Core (Broad Range) | Denier of Cabled Core (Preferred Range) |
|---|---|---|---|
| greater than about 125 to about 200 | 6/0 | 20–80 | 25–50 |
| greater than about 200 to about 300 | 5/0 | 30–100 | 50–80 |
| greater than about 300 to about 500 | 4/0 | 80–150 | 80–120 |
| greater than about 500 to about 800 | 3/0 | 150–300 | 180–280 |
| greater than about 800 to about 1200 | 2/0 | 250–700 | 350–650 |
| greater than about 1200 to about 2000 | 0 | 400–1200 | 500–1000 |
| greater than about 2000 to about 4000 | 1,2 | 800–2400 | 1000–2200 |

Based on the foregoing, for a given preferred suture construction of a particular overall suture denier, the range of pick count, number of sheath yarns, denier of individual filaments and denier of the cabled core are related to each other as follows:

TABLE IV

Braided Suture Construction Parameters

| Overall Suture Denier | Pick Count | Number of Sheath Yarns | Denier of Individual Filaments | Denier of Cabled Core |
|---|---|---|---|---|
| greater than about 125 to about 200 | from about 50 to about 100 | from about 4 to about 16 | from about 0.2 to about 1.8 | 20–80 |
| greater than about 200 to about 300 | from about 50 to about 100 | from about 4 to about 16 | from about 0.2 to about 1.8 | 30–100 |
| greater than about 300 to about 500 | from about 50 to about 100 | from about 10 to about 20 | from about 0.2 to about 6.0 | 80–150 |
| greater than about 500 to about 800 | from about 50 to about 100 | from about 14 to about 20 | from about 0.2 to about 6.0 | 150–300 |
| greater than about 800 to about 1200 | from about 50 to about 100 | from about 16 to about 32 | from about 0.2 to about 6.0 | 250–700 |
| greater than about 1200 to about 2000 | from about 50 to about 100 | from about 20 to about 36 | from about 0.2 to about 6.0 | 400–1200 |
| greater than about 2000 to about 4000 | from about 50 to about 100 | from about 20 to about 36 | from about 0.2 to about 6.0 | 800–2400 |

In yet a more preferred braided suture construction, the relationship of the structural elements of the suture for a given suture size is set forth in Table V as follows:

TABLE V

More Preferred Braided Suture Construction Parameters

| Overall Suture Denier | Pick Count | Number of Sheath Yarns | Denier of Individual Filaments | Denier of Cabled Core |
|---|---|---|---|---|
| greater than about 125 to about 200 | from about 55 to about 80 | from about 6 to about 14 | from about 0.8 to about 1.8 | 25–50 |
| greater than about 200 to about 300 | from about 55 to about 80 | from about 6 to about 14 | from about 0.8 to about 1.8 | 50–80 |
| greater then about 300 to about 500 | from about 55 to about 80 | from about 12 to about 14 | from about 0.8 to about 3.0 | 80–120 |
| greater than about 500 to about 800 | from about 55 to about 80 | from about 14 to about 18 | from about 0.8 to about 3.0 | 180–280 |
| greater than about 800 to about 1200 | from about 55 to about 80 | from about 20 to about 30 | from about 0.8 to about 3.0 | 350–650 |
| greater than about 1200 to about 2000 | from about 55 to about 80 | from about 24 to about 32 | from about 0.8 to about 3.0 | 500–1000 |
| greater than 2000 to about 4000 | from about 55 to about 80 | from about 24 to about 32 | from about 0.8 to about 3.0 | 1000–2200 |

For larger sutures, i.e. sutures having an overall suture denier greater than about 300, the range of pick count, number of sheath yarns, denier of individual filaments and denier of the cabled core are related to each other as follows:

TABLE VI

Braided Suture Construction Parameters

| Overall Suture Denier | Pick Count | Number of Sheath Yarns | Denier of Individual Filaments | Denier of Cabled Core |
|---|---|---|---|---|
| greater than about 300 to about 500 | from about 50 to about 100 | from about 10 to about 20 | from about 0.2 to about 6.0 | 80–150 |
| greater than about 500 to about 800 | from about 50 to about 100 | from about 14 to about 20 | from about 0.2 to about 6.0 | 150–300 |
| greater than about 800 to about 1200 | from about 50 to about 100 | from about 16 to about 32 | from about 0.2 to about 6.0 | 250–700 |
| greater than about 1200 to about 2000 | from about 50 to about 100 | from about 20 to about 36 | from about 0.2 to about 6.0 | 400–1200 |
| greater than about 2000 to about 4000 | from about 50 to about 100 | from about 20 to about 36 | from about 0.2 to about 6.0 | 800–2400 |

In a more preferred braided suture construction of larger overall denier, the relationship of the structural elements of the suture for a given suture size is set forth in Table VII as follows:

TABLE VII

More Preferred Braided Suture Construction Parameters

| Overall Suture Denier | Pick Count | Number of Sheath Yarns | Denier of Individual Filaments | Denier of Cabled Core |
|---|---|---|---|---|
| greater than about 300 to about 500 | from about 55 to about 80 | from about 12 to about 14 | from about 0.8 to about 3.0 | 80–120 |
| greater than about 500 to about 800 | from about 55 to about 80 | from about 14 to about 18 | from about 0.8 to about 3.0 | 180–280 |
| greater than | from about 55 | from about 20 | from about 0.8 | 350–650 |

TABLE VII-continued

More Preferred Braided Suture Construction Parameters

| Overall Suture Denier | Pick Count | Number of Sheath Yarns | Denier of Individual Filaments | Denier of Cabled Core |
|---|---|---|---|---|
| about 8CO to about 1200 | to about 80 | to about 30 | to about 3.0 | |
| greater than about 1200 to about 2000 | from about 55 to about 80 | from about 24 to about 32 | from about 0.8 to about 3.0 | 500–1000 |
| greater than about 2000 about 4000 | from about 55 to about 80 | from about 24 to about 32 | from about 0.8 to about 3.0 | 1000–2200 |

As a result of their possessing a greater pick count and/or a greater number of sheath yarns for a suture of given overall denier and in some cases, a finer denier for the individual filaments making up a sheath yarn, the braided sutures of Tables IV–VII exhibit far fewer surface discontinuities, thereby providing sutures which are considerably smoother than braided sutures of known construction.

It can be advantageous to apply one or more coating compositions to the braided suture of this invention to improve such properties as surface lubricity, knot tiedown behavior, and so forth. A variety of suture coating compositions proposed for either or both purposes is known in the art, e.g., those disclosed in U.S. Pat. No. 4,047,53.

It is also within the scope of this invention to impregnate the suture with, or otherwise apply thereto, one or more medico-surgically useful substances, e.g., those which accelerate or beneficially modify the healing process when the suture is applied to a wound or surgical site. So, for example, the braided suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamycin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or several growth promoting factors can be introduced into the suture, e.g., human growth factors such as fibroblast growth factor, bone growth factor, epidermal growth factor, platelet-derived growth factor, macrophage-derived growth factor, alveolar-derived growth factor, monocyte-derived growth factor, magainin, carrier proteins, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

The following examples are illustrative of the braided suture of the invention. In all cases, the suture filaments were constructed from a 90–10 weight percent glycolide-L-lactide copolymer.

EXAMPLES 1–4

The cabled cores of Examples 1–4 were constructed in accordance with the parameters set forth in Table VIII as follows:

TABLE VIII

Cabled Core Construction Characteristics

| Example | No. of Filaments In The Core | Denier of Individual Yarns In The Core | No. of Yarns In Each Plied Yarn | First Twist In Turns Per Meter (applied to the plied yarn) | Second Twist In Turns Per Meter (applied to form the core) | Coefficient of Twist | Cabled Core Denier |
|---|---|---|---|---|---|---|---|
| 1[a] | 60 × 7 × 3 | 72 | 7 | 305 | 250 | 32 | 1512 |
| 2 | 35 × 7 × 3 | 42 | 7 | 534 | 409 | 40 | 882 |
| 3 | 22 × 7 × 3 | 26 | 7 | 583 | 447 | 35 | 554 |
| 4 | 28 × 3 × 3 | 33 | 3 | 823 | 630 | 37 | 297 |

[a]see formula (2) supra

Braided sutures were constructed around the cabled cores of Examples 1–4 in accordance with the parameters set forth in Table IX as follows:

TABLE IX

Braided Suture Construction Characteristics

| Core of Example | Suture Size | Overall Suture Denier | Pick Count | No. of Sheath Yarns | Denier of Individual Yarns Sheath | Core | % of Core | Braid Angle |
|---|---|---|---|---|---|---|---|---|
| 1 | 1 | 2280 | 74 | 32 | 24 | 70 | 66 | 15.3 |
| 2 | 1/0 | 1550 | 80 | 28 | 24 | 40 | 57 | 17.4 |
| 3 | 2/0 | 1130 | 72 | 24, | 24 | 24 | 49 | 15.4 |
| 4 | 3/0 | 650 | 58 | 16 | 24 | 30 | 41 | 13.7 |

In no case did core popping occur with any of the foregoing sutures thus demonstrating the effectiveness of the cabled core in restraining any tendency of the core to penetrate the external sheath during handling of the suture.

EXAMPLES 5–11

The cabled cores of Examples 5–11 were constructed in accordance with the parameters set forth in Table X as follows:

COMPARATIVE EXAMPLES 12–16

The cabled cores of Comparative Examples 12–16 were constructed in accordance with the parameters set forth in Table XII as follows:

TABLE X

Cabled Core Construction Characteristics

| Example | No. of Filaments In The Core | Denier of Individual Yarns In Core | Denier Of Each Plied Yarn | Total Core Denier | Front Twist In Turns Per Meter Applied To Each Plied Yarn[b] | Back Twist In Turns Per Meter To Form Cable Core | Coefficient Of Back Twist |
|---|---|---|---|---|---|---|---|
| 5 | 69 × 7 × 3 | 110 | 770 | 2,310 | 250 | 278 | 44.5 |
| 6 | 48 × 7 × 3 | 77 | 540 | 1,617 | 320 | 324 | 43.5 |
| 7 | 27 × 7 × 3 | 43 | 300 | 900 | 590 | 505 | 50.5 |
| 8 | 17 × 7 × 3 | 27 | 190 | 570 | 640 | 576 | 45.8 |
| 9 | 54 × 1 × 3 | 86 | 86 | 258 | 830 | 854 | 45.7 |
| 10 | 23 × 1 × 3 | 37 | 37 | 110 | 1,000 | 1,05 | 36.3 |
| 11 | 17 × 1 × 3 | 27 | 27 | 80 | 1,200 | 1,200 | 36.0 |

[b]In Examples 9, 10 and 11, only unplied yarn was used

Braided sutures were constructed around the cabled cores of Examples 5–11 in accordance with the parameters set forth in Table XI as follows:

TABLE XI

Braided Suture Construction Characteristics

| Core of Example | Suture Size | Overall Suture Denier | Pick Count Picks Per Inch | No. of Sheath Yarns | Denier of Sheath/Core | | % of Core | Braid Angle |
|---|---|---|---|---|---|---|---|---|
| 5 | 2 | 3,190 | 79 | 32 | 870 | 2,320 | 73 | 18 |
| 6 | 1 | 2,380 | 79 | 32 | 770 | 1,610 | 68 | 18 |
| 7 | 0 | 1,580 | 83 | 28 | 670 | 910 | 58 | 17 |
| 8 | 2/0 | 1,150 | aB | 24 | 580 | 570 | 50 | 17 |
| 9 | 3/0 | 690 | 63 | 16 | 430 | 260 | 38 | 16 |
| 10 | 4/0 | 440 | 79 | 12 | 330 | 110 | 25 | 16 |
| 11 | 5/0 | 300 | 55 | 8 | 220 | 80 | 27 | 15 |

TABLE XII

Cabled Core Construction Parameters

| Comparative Example | No. of Filaments In The Core | Denier of Yarns In Each Ply[c] | No. Of Yarns In Each Ply[c] | First Twist In Turns Per Meter (applied to each plied yarn)[c] | Second Twist In Turns Per Meter (applied to the core) | Coefficient of Twist | Cabled Core Denier |
|---|---|---|---|---|---|---|---|
| 12 | 110 × 3 × 3 | 132 | 3 | 193 | 120 | 14 | 1188 |
| 13 | 60 × 3 × 3 | 70 | 3 | 438 | 257 | 22 | 648 |
| 14 | 50 × 3 × 3 | 60 | 3 | 193 | 85 | 7 | 540 |
| 15 | 50 × 3 × 3 | 60 | 3 | 193 | 85 | 7 | 540 |
| 16 | 60 × 1 × 3 | 70 | 1 | 560 | 430 | 21 | 216 |

[c]In Comparative Example 16, only unplied yarn was used

Braided sutures were constructed around the cores of Comparative Examples 12–16 in accordance with the parameters set forth in Table XIII as follows:

TABLE XIII

Braided Suture Construction Characteristics

| Core of Comparative Example | Suture Size | Overall Suture Denier | Pick Count | No. of Sheath Yarns | Denier of Individual Yarns Sheath | Denier of Individual Yarns Core | % of Core | Braid Angle |
|---|---|---|---|---|---|---|---|---|
| 12 | 1 | 1960 | 79 | 32 | 24 | 132 | 60 | 15.7 |
| 13 | 1/0 | 1320 | 74 | 2B | 24 | 72 | 49 | 15.6 |
| 14 | 2/0 | 1120 | 86 | 24 | 24 | 60 | 48 | 20.0 |
| 15 | 2/0 | 1120 | 78 | 24 | 24 | 60 | 48 | 17.5 |
| 16 | 3/0 | 600 | 80 | 16 | 24 | 72 | 36 | 14.8 |

In every case core popping was observed. This appears to have been due to low coefficient of twist (below 24).

What is claimed is:

1. In a braided suture, the improvement comprising a core made of yarns twisted in a first direction, said twisted yarns being twisted together in a second direction to form a core having a coefficient of twist in said second direction of at least about 24, wherein the coefficient of twist of the core, alpha, in said second direction is determined from the equation:

$$\text{alpha} = \frac{K}{100} \sqrt{0.111 D}$$

where:

K=twist level in turns per meter; and
D=denier of the core.

2. The core of claim 1 wherein said core has a coefficient of twist of at least about 28.

3. The core of claim 2 wherein said core has a coefficient of twist of at least about 32.

4. The core of claim 1 wherein said yarns possess a twist having a coefficient of twist substantially equal to but opposite the coefficient of twist in said second direction.

5. The core of claim 1 wherein said yarns are fabricated from a non-absorbable material.

6. The core of claim 5 wherein said non-absorbable material is cotton, silk, polyamide or polyolefin.

7. The core of claim 1 wherein said yarns are fabricated from a bioabsorbable material.

8. The core of claim 7 wherein said yarns are fabricated from a polymer derived at least in part from one or more monomers selected from the group consisting of glycolic acid, glycolide, lactic acid and lactide.

9. The core of claim 1 wherein the core is constructed form a plurality of individual yarns possessing a first twist of from about 100 to about 1500 turns per meter, the twisted yarns being assembled into a core possessing a second, opposite twist of from about 100 to about 1200 turns per meter.

10. The core of claim 9 wherein the core is constructed from a plurality of individual yarns possessing a first twist of from about 200 to about 1200 turns per meter, the twisted yarns being assembled into a core possessing a second, opposite twist of from about 300 to about 1100 turns per meter.

11. The core of claim 1 wherein said twisted yarns are plied prior to said second twist.

12. The core of claim 1 wherein the overall suture denier and the denier of the core are related as follows:

| OVERALL SUTURE DENIER | DENIER OF CORE |
|---|---|
| greater than about 125 to about 200 | 20–80 |
| greater than about 200 to about 300 | 30–100 |
| greater than about 300 to about 500 | 80–150 |
| greater than about 500 to about 800 | 150–300 |
| greater than about 800 to about 1200 | 250–700 |
| greater than about 1200 to about 2000 | 400–1200 |
| greater than about 2000 to about 4000 | 800–2400 |

13. The core of claim 12 wherein the overall suture denier and the denier of the core are related as follows:

| OVERALL SUTURE DENIER | DENIER OF CORE |
|---|---|
| greater than about 125 to about 200 | 25–50 |
| greater than about 200 to about 300 | 50–80 |
| greater than about 300 to about 500 | 80–120 |
| greater than about 500 to about 800 | 180–280 |
| greater than about 800 to about 1200 | 350–650 |
| greater than about 1200 to about 2000 | 500–1000 |
| greater than about 2000 to about 4000 | 1000–2200 |

14. In a braided suture, the improvement Comprising a core made of yarns twisted in a first direction, said twisted yarns being twisted together in a second direction to form a core having a coefficient of twist in said second direction of at least about 24, wherein the overall suture denier and the denier of the core are related as follows:

| OVERALL SUTURE DENIER | DENIER OF CORE |
|---|---|
| greater than about 125 to about 200 | 20–80 |
| greater than about 200 to about 300 | 30–100 |
| greater than about 300 to about 500 | 80–150 |
| greater than about 500 to about 800 | 150–300 |
| greater than about 800 to about 1200 | 250–700 |
| greater than about 1200 to about 2000 | 400–1200 |
| greater than about 2000 to about 4000 | 800–2400 |

15. The core of claim 14 wherein the overall suture denier and the denier of the core are related as follows:

| OVERALL SUTURE DENIER | DENIER OF CORE |
|---|---|
| greater than about 125 to about 200 | 25–50 |
| greater than about 200 to about 300 | 50–80 |
| greater than about 300 to about 500 | 80–120 |
| greater than about 500 to about 800 | 180–280 |
| greater than about 800 to about 1200 | 350–650 |
| greater than about 1200 to about 2000 | 500–1000 |
| greater than about 2000 to about 4000 | 1000–2200 |

16. The core of claim 14 wherein said core has a coefficient of twist of at least about 28.

17. The core of claim 16 wherein said core has a coefficient of twist of at least about 32.

18. The core of claim 14 wherein the coefficient of twist of the core, alpha, is determined from the equation:

$$\text{alpha} = \frac{K}{100} \sqrt{0.111D}$$

where:
K=twist level in turns per meter; and
D=denier of the core.

19. The core of claim 14 wherein said yarns possess a twist having a coefficient of twist substantially equal to but opposite the coefficient of twist in said second direction.

20. The core of claim 14 wherein said yarns are fabricated from a non-absorbable material.

21. The core of claim 20 wherein said non-absorbable material is cotton, silk, polyamide or polyolefin.

22. The core of claim 14 wherein said yarns are fabricated from a bioabsorbable material.

23. The core of claim 22 wherein said yarns are fabricated from a polymer derived at least in part from one or more monomers selected from the group consisting of glycolic acid, glycolide, lactic acid and lactide.

24. The core of claim 14 wherein the core is constructed from a plurality of individual yarns possessing a first twist of from about 100 to about 1500 turns per meter, the twisted yarns being assembled into a core possessing a second, opposite twist of from about 100 to about 1200 turns per meter.

25. The core of claim 24 wherein the core is constructed from a plurality of individual yarns possessing a first twist of from about 200 to about 1200 turns per meter, the twisted yarns being assembled into a core possessing a second, opposite twist of from about 300 to about 1100 turns per meter.

26. The core of claim 14 wherein said twisted yarns are plied prior to said second twist.

27. A method of making a core for a braided suture comprising:
 (i) twisting yarns in a first direction; and,
 (ii) twisting at least two of said twisted yarns together in a second direction opposite said first direction to form a core having a coefficient of twist in said second direction of at least about 24,
 wherein the coefficient of twist of said core, alpha, in said second direction is determined from the equation:

$$\text{alpha} = \frac{K}{100} \sqrt{0.111D}$$

where:
K=twist level in turns per meter; and
D=denier of the core.

28. The method of claim 27 wherein said step of twisting yarns comprises twisting said yarns to possess of coefficient of twist in said first direction substantially equal to the coefficient of twist in said second direction.

29. The method of claim 27 wherein the coefficient of twist of the core is at least about 28.

30. The method of claim 29 wherein the coefficient of twist of the core is at least about 32.

31. The method of claim 27 wherein said step of twisting yarns comprises twisting said yarns in said first direction from about 100 to about 1500 turns per meter.

32. The method of claim 27 wherein said step of twisting yarns comprises twisting sad yarns in said first direction from about 200 to about 1200 turns per meter.

33. The method of claim 27 wherein said step of twisting in a second direction comprises twisting said twisted yarns from about 100 to 1200 turns per meter.

34. The method of claim 27 wherein said step of twisting in a second direction comprises twisting said twisted yarns from about 300 to about 1100 turns per meter.

35. The method of claim 27 further comprising the step of braiding yarns around said cabled core to form a suture.

36. A method of making a cabled core for a braided suture comprising:

(i) plying at least two yarns together without twisting said yarns to form plied yarns;

(ii) twisting said plied yarns in a first direction; and, (iii) twisting a plurality of said twisted plied yarns together in a second direction opposite said first direction to form a cabled core;

wherein said step of twisting in a second direction comprises twisting in said second direction so as to provide a coefficient of twist of the core, in said second direction, of at least about 24, and the coefficient of twist of said core, alpha, in said second direction is determined from the equation:

$$\text{alpha} = \frac{K}{100} \sqrt{0.111D}$$

where:

K=twist level in turns per meter; and

D=denier of the core.

37. The method of claim 36 further comprising braiding sheath yarns around said core to form a braided suture product.

38. A core for a braided suture comprising individual yarns plied together, said plied yarns being twisted together in a first direction, and multiple twisted plied yarns being twisted together in a second direction to form a cabled core.

wherein said individual yarns are plied together before twisting in said first direction and said core has a coefficient of twist in said second direction of at least about 24, and the coefficient of twist of said core, alpha, in said second direction is determined from the equation:

$$\text{alpha} = \frac{K}{100} \sqrt{0.111D}$$

where:

K=twist level in turns per meter; and

D=denier of the core.

39. The core of claim 38 wherein said twisted yarns have a coefficient of twist in said first direction substantially equal to the coefficient of twist in said second direction.

* * * * *